(12) United States Patent
Kasper et al.

(10) Patent No.: US 10,744,029 B1
(45) Date of Patent: Aug. 18, 2020

(54) ANIMAL COOLING KIT

(71) Applicants: Leslie Melville Kasper, Milton, GA (US); Olivia Melville Kasper, Milton, GA (US); McKenzie Eleanor Kasper, Milton, GA (US)

(72) Inventors: Leslie Melville Kasper, Milton, GA (US); Olivia Melville Kasper, Milton, GA (US); McKenzie Eleanor Kasper, Milton, GA (US)

(*) Notice: Subject to any disclaimer, the term of this patent is extended or adjusted under 35 U.S.C. 154(b) by 95 days.

(21) Appl. No.: 15/785,007

(22) Filed: Oct. 16, 2017

(51) Int. Cl.
*A61F 7/00* (2006.01)
*A61F 7/10* (2006.01)
*A01K 13/00* (2006.01)

(52) U.S. Cl.
CPC .......... *A61F 7/0097* (2013.01); *A01K 13/006* (2013.01); *A01K 13/008* (2013.01); *A61F 7/10* (2013.01); *A61F 2007/0009* (2013.01); *A61F 2007/0056* (2013.01)

(58) Field of Classification Search
CPC .... A61F 7/0097; A01K 13/006; A01K 13/008
See application file for complete search history.

(56) References Cited

U.S. PATENT DOCUMENTS

| | | | |
|---|---|---|---|
| 9,386,759 B2* | 7/2016 | Russakoff | A01K 13/008 |
| 2002/0043218 A1* | 4/2002 | Butler | A01K 13/008 |
| | | | 119/792 |
| 2010/0050958 A1* | 3/2010 | Jackson | A01K 13/006 |
| | | | 119/850 |
| 2014/0358205 A1* | 12/2014 | Robke | A61D 1/00 |
| | | | 607/109 |

FOREIGN PATENT DOCUMENTS

GB 2399483 A * 9/2004 ........... A01K 13/008

OTHER PUBLICATIONS

Baptiste, K.E., Naylor, J.M., A Function for Guttural Pouches in the Horse. Nature, vol. 403, 2000, 382-383.

* cited by examiner

*Primary Examiner* — Kristen Matter (57) ABSTRACT

The combined members potentiate the autonomic, thermoregulation of an animal such as a horse. An absorbent wrap cools an animal by removing its extra heat during extreme physical and environmental conditions. The wrap member is submerged in water, excess moisture removed, then placed in a sealed, insulated cooler lined with frozen icepacks where the components stay cold until use. The wrap is removed from the cooler and seen in one embodiment fitted around the neck of an animal and held in place by fasteners. Temperature remediation occurs through a countercurrent exchange where incoming and outgoing elements touch to remove heat. The cooling wrap increases an animal's physiological mechanisms by working with their vascular structures and respiratory tract during selective brain cooling (SBC). The animal while stationary or under movement is cooled through the processes of conductive, evaporative and circulatory cooling.

10 Claims, 5 Drawing Sheets

ANIMAL COOLING KIT

CROSS-REFERENCE TO RELATED APPLICATIONS

Not Applicable

STATEMENT REGARDING FEDERALLY SPONSORED RESEARCH AGREEMENT Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXTFILE VIA THE OFFICE ELECTRONIC FILING SYSTEM (EFS-WEB)

Not Applicable

STATEMENT REGARDING PRIOR DISCLOSURES BY THE INVENTOR OR JOINT INVENTOR

Not Applicable

TECHNICAL FIELD

The present invention relates generally to large mammals such as horses, and more specifically to a device that decreases the temperature of a large animal through cooling.

BACKGROUND OF THE INVENTION

A large animal such as a horse has a good deal of body mass. An average size horse can weigh over 1400 lbs. Under normal conditions a horse does not require external assistance with thermoregulation. However, in instances of extremely hot and or humid environmental conditions, great physical exertion, and during illness, horses and other quadrupeds can generate a lot of extra body heat that can become life threatening if not properly managed. Hyperthermia, also known as heat stroke is a dangerous condition whereby a horse is unable to lose body heat, and its body temperature goes up rapidly causing severe health concerns that can result in an unsafe drop in blood sugar, colic, muscular denaturation (cooking), renal failure and or fatality. Consequently, untreated excessive heat has a destructive effect on the cells of all equine tissue, and is particularly important with regards to the brain. In the case of a domestic large animal like the horse, it is the responsibility of the caretaker to ensure the safety and wellbeing of the animal through the best means available, sometimes under less than optimal circumstances. The goal is to safely cool the horse. Successful heat removal can be accomplished by methods of radiation, convection, evaporation, and conduction with some techniques being more effective than others when dealing with horses.

Original evaporative cooling interventions include dousing an overheated horse repeatedly with buckets of ice water spread over their back, neck and legs, and using a tool to serve as a scraper to rapidly wipe away the water from the surface area of the horse as the water becomes heated. Unfortunately the water applied under this method heats up almost instantaneously, and therefore requires rapid scraping followed by the application of more iced water. This sequence continues until there is a change in in the horse's core temperature. This protocol serves as a cumbersome challenge since above and beyond the person-power involved, having enough ice readily available to significantly cool the water takes planning, not to mention that even with access to ice, enough water is not always easily available and or transportable on long rides away from home, during hauling in a hot trailer, shipping by airplane, with unforeseen illness, or at the competition arena with a post-competition horse wearing full tack, or equestrian gear.

Convective heat loss used for equine cooling, is accomplished through the movement of air around a horse that is of a lesser temperature than the core temperate of the horse. However, as the air temperature circulating around the horse becomes close to its body temperature, actual heat loss due to convection rapidly declines until the ambient temperature equals the horse body temperature and convection heat loss ceases. Additionally, the electricity necessary for some standard, prior art cooling devices such as a conventional fan, portable air conditioner, or water misting machine makes things equally difficult when a horse unexpectedly presents as hyperthermic in a rural environment, or while in transit void of utilities, or in the show ring where a natural breeze is not to be relied upon and fans are seldom provided.

Prior art Russakoff and Campbell, U.S. Pat. No. 9,386,759, Jul. 12, 2016 discloses a towel with an elaborate fastening system for the management of heat stress that fits over a large animal such as a horse. According to detailed description, this art requires vigorous, and periodic flapping to continually ensure support of its evaporative nature. Regardless of which portion of the horse the disclosed towel covers, the requirement of flapping by design is inconvenient at best and at worst, a dangerous necessity when dealing with a hot, very large prey animal with an instinctual fight or flight defense mechanism. The need to vigorously wave an article of fabric manually or artificially, that is attached with a buckle assembly to an already compromised 1400 lb animal is dicey and puts the caretaker at risk of injury if the horse attempts to flee, as well as further stresses the animal by raising its anxiety with the compulsory fabric agitation. Alternatively, using a fan and therefore needing the necessary electricity (or gas and generator) to run a piece of equipment to assist with vigorous flapping makes this towel as inconvenient as the above mentioned, original interventions. Lastly, this prior art of evaporative cooling will not fare well when the relative humidity is high outside. When the ambient water vapor pressure approaches that of the moist surface of the towel/skin evaporation is impeded.

What is needed is an invention that solves the requirement of effectively cooling a large animal like a horse after exercise, travel and or during fever from illness, while overcoming the aforementioned disadvantages of constant movement, electricity, water, ice, extra person-power and cumbersome devices.

Separate from heat stress, is the issue of sickness and the associated hurdles a caretaker must overcome to effectively reduce the core temperature of an ill animal. The horse is an exceptionally designed, athletic animal that must keep their brain cool during exertion and illness. Typically, the normal rectal temperature for a healthy, adult horse is between the range of 99.5-101 degrees Fahrenheit, with alert, active and responsive reactions to noise and visual stimuli, good appetite and ample fluid intake. However, while sick or injured, a horse's temperature can elevate well past the high end of the normal range of rectal temperatures to as high as 107 degrees Fahrenheit.

Symptoms of a febrile horse include a general malaise and lethargy, loss of appetite, reduction of water intake, decrease in urine and manure output and a reduction or absence of normal gut sounds associated with healthy intestinal movement and digestive functions, which are key components to a well horse. Horses, unlike other quadrupeds are non-emetic, and therefore cannot throw-up when sick. As a naturally grazing species, the sensitive digestive tract of horses is designed for and requires constant grazing. Severe complications for a horse can arise in connection with a fever that lasts for more than a couple of days, when the impact of the fever creates a loss of appetite, a decrease in consumption, and or dehydration.

Traditional treatment and prior art for high equine fevers over 104 degrees Fahrenheit due to illness, include pharmacological intervention such as non-steroidal anti-inflammatory drugs, and a cold bath with thorough and continual scraping to remove the warmed excess water. Unfortunately, prior art solutions involving the use of person-power for scraping cold water is cumbersome and exhaustive as stated above, not to mention not always accessible or effective when used by itself. The use of antipyretic medication for the treatment of fever has potentially undesirable consequences for the horse such as gastrointestinal ulcers and renal complications. Regardless, as will be addressed, there are times when drugs do not work to reduce a fever.

Jonathan Naylor, BVSc, PHD, Dipl. ACVIM and Keith Baptiste BUMS, MSc, PhD, DACVIM both theorized and successfully tested their hypotheses, that there was more to equine thermoregulation that involved the equine guttural pouches. The guttural pouches are bilateral, fist-sized cavities located in the horse's skull, which sit slightly behind the ears. Each guttural pouch contains 300-500 ml of air and functions autonomously during selective brain cooling. Accordingly, Drs. Baptiste and Naylor believed that respiratory and circulatory functions of a healthy horse naturally serve to maintain cooler air in the guttural pouches, thus cooling the blood supply carried within the vascular network associated around and within the guttural pouches, ultimately leading to the brain working to achieve a cooler core temperature.

Extensive testing by Naylor and Baptiste discovered that in heavily exercised, otherwise healthy horses, (meaning horses that engaged in cantering at between 10-17 miles per hour for five uninterrupted minutes, the blood leaving the guttural pouches was an average of three degrees Fahrenheit cooler than the blood that arrived at the location where the vascular system entered the guttural pouch. This was a drop from 103.1 degrees Fahrenheit to 100.04 degrees Fahrenheit. Although a significant finding, a post-exercise, healthy equine temperature of 103.1 degrees Fahrenheit is not as alarming as the core temperature of a sick horse reaching 107 degrees Fahrenheit during heat stroke or illness. As such, an invention that helps cool a hot horse without disadvantages is needed.

BRIEF SUMMARY OF THE INVENTION

In an exemplary representation and without limitation thereof, the animal cooling kit having a preferred animal cooling wrap, an insulated cooler and an icepack, solves one or more of the problems set forth above. The animal cooling wrap comprises one or more, three-dimensional, water-absorbent, open-cell, foam-structured, gas-permeable panels, with a plurality of removable elastic straps and releasable closures. The panels are comprised of material having a top side facing away from the animal with a smooth texture, and a bottom side touching the animal having a plurality of uniform-sized, concave orifices of a spherical form, (dimples). Although the structure of the dimples is curved inward, thus away from the subject and towards the top side of the material, the remainder of the bottom side surrounding the dimples is smooth in texture, and conversely does by design come in direct contact with the animal.

Water is applied to both the top and bottom sides of the absorbent wrap and wrung out, and the wrap placed in the standard insulated cooler which serves to house the standard frozen icepacks which have received a suitable amount of cold temperature from a standard freezer. The cold icepacks transfer cold temperature to the material of the animal cooling wrap through conduction. The cold animal cooling wrap is placed over the animal, and in one embodiment covers the dorsal and the ventral sections of the neck of a horse, in an uninterrupted piece of material. The panels are kept in contact with the anatomical body parts associated with selective brain cooling of the horse, by a plurality of removable elastic straps and releasable closures creating a contoured and continuous panel of material, which maximizes the cooling effect through a countercurrent exchange circuit between the horse and the animal cooling wrap involving conductive, evaporative and circulatory cooling.

DETAILED DESCRIPTION OF THE INVENTION

An animal cooling kit, according to the invention potentiates the existing thermoregulation of quadrupeds such as a horse, by supercharging the unique anatomical arrangements of an animal that contribute to their selective brain cooling. The invention by design maximizes this autonomic brain cooling system through a process of temperature reduction that includes a cold animal cooling wrap, which provokes a countercurrent exchange circuit for conductive, evaporative and circulatory cooling. Accordingly, the symptoms and conditions associated with hyperthermia and with high core temperatures linked with fever are addressed. Based upon the aforementioned research of Drs. Naylor and Baptiste, the research findings described in "A Function for Guttural Pouches in the Horse", (Nature. 2000 Jan. 27; p. 382-3), are used only for the exemplary purpose of one type of animal, a horse, and one or more anatomical body parts associated with cooling, namely the guttural pouches so as to illustrate principle. The invention claimed, unlimited by shape or design will, according to principle potentiate the internal cooling role of specialized anatomical body parts found in horses and other large quadrupeds, during the process of selective brain cooling.

The combination of members in the preferred but not restricted embodiment and mode of operation of the animal cooling kit describes its use on a horse, and involves an ice-cold animal cooling wrap created by immersing the absorbent animal cooling wrap material of three-dimensional, porous construct in water, wringing out the excess moisture and placing it indirectly upon the frozen icepack that has been removed from a standard freezer of preferred temperature range between 0 and 10 degrees Fahrenheit, (but any suitable temperature outside of this preferred range will work), and placed in the insulated cooler which by its standard nature is an encasement representing materials that make for a poor conductor of heat.

The ice pack can be fabricated out of (but not restricted to) a portable sac filled with water, or refrigerant gel, or other liquid, and is extended to include any other means such as frozen carbon dioxide gas, or self-contained refrigerant pockets cooled by standard low-voltage or standard electrical components, through which the process of thermodynamics, the animal cooling wrap can be made cold to a preferred range between 50-55 degrees Fahrenheit, but any suitable range of temperature will work.

When the cold animal cooling wrap member of the animal cooling kit is placed upon a hot horse and held in position without slipping or leaving connection with the animal, it triggers a conductive exchange of heat from the hot horse to the cold animal cooling wrap, and facilitates cooling of the horse in the countercurrent exchange circuit. The panels of the exemplary animal cooling wrap according to the invention and not restricted to shape or size, when adjusted to the horse, are contoured to the shape of the animal, covering the anatomical body part(s) associated with cooling. These anatomical body parts including but not limited to the guttural pouches, and the major vascular network system, are secured by a plurality of straps and hook assemblies that keep the wrap from lifting off the body of the horse. The cold animal cooling wrap is kept constantly upon the surface area of the horse, and specifically over the anatomical body parts associated with autonomic selective brain cooling, and serves to facilitate a continuous conductive, evaporative and circulatory heat exchange between the horse and the cold animal cooling wrap, while the horse is either stationary or under locomotion, supervised by a caretaker or independent thereof.

The animal cooling kit as such is designed upon requirements anatomically related, hereafter described, and will, for exemplary purpose only, be assumed preferred for a horse, and shall include but not be limited to: an animal cooling wrap, ice pack and an insulated cooler.

Figure 1A:
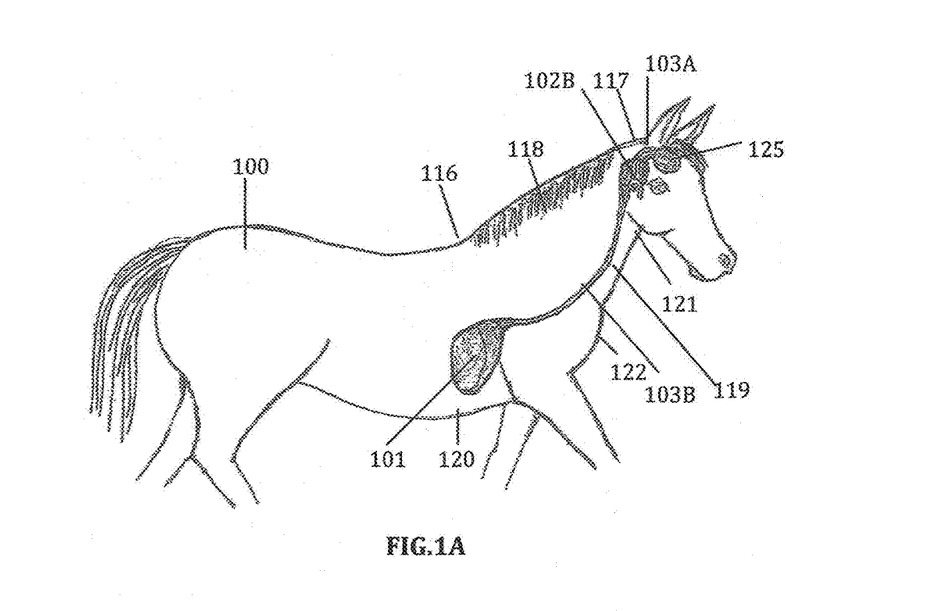
FIG. 1A is a right side view of a horse wherein anatomical body parts are shown.

FIG. 1A is a right side view of a horse, 100 where a heart 101 connects to a right guttural pouch 102B by a vascular connection 103B which also is embedded in the surface and interior of the guttural pouch, 102B, exiting as a vascular connection, 103A, and continuing to a brain, 125. Also depicted area withers 116, a poll 117, a right dorsal neck section, 118, a right ventral neck section, 119, a barrel, 120, a throat latch, 121, and a chest, 122.

Figure 1B:
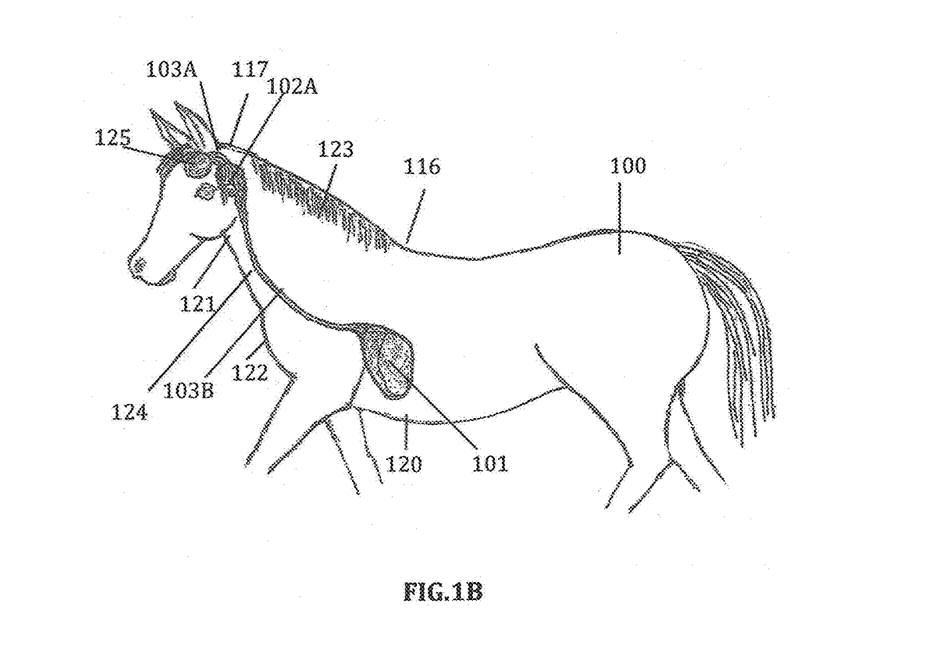
FIG. 1B is a left side view of a horse wherein anatomical body parts are shown.

FIG. 1B is a left side view of the horse, 100 where the heart 101 connects to a left guttural pouch 102A by vascular connection 103B which also is embedded in the surface and interior of guttural pouch, 102A, exiting as vascular connection, 103A, and continuing to the brain, 125. Also depicted are the withers 116, the poll 117, a left dorsal neck section, 123, a left ventral neck section, 124, the barrel, 120, the throat latch, 121, and the chest, 122.

From an anatomical perspective, one skilled in the art will notice the close proximity of the guttural pouches 102B, FIG. 1A and 102A, FIG. 1B to the brain 125 of horse, 100, as well as the internal vascular network(s), 103A and 103B of the neck and head, in horse 100, FIGS. 1A and 1B. Accordingly, as features and aspects of the invention are further illustrated in the figures, several advantages will be made clear.

Figure 2:
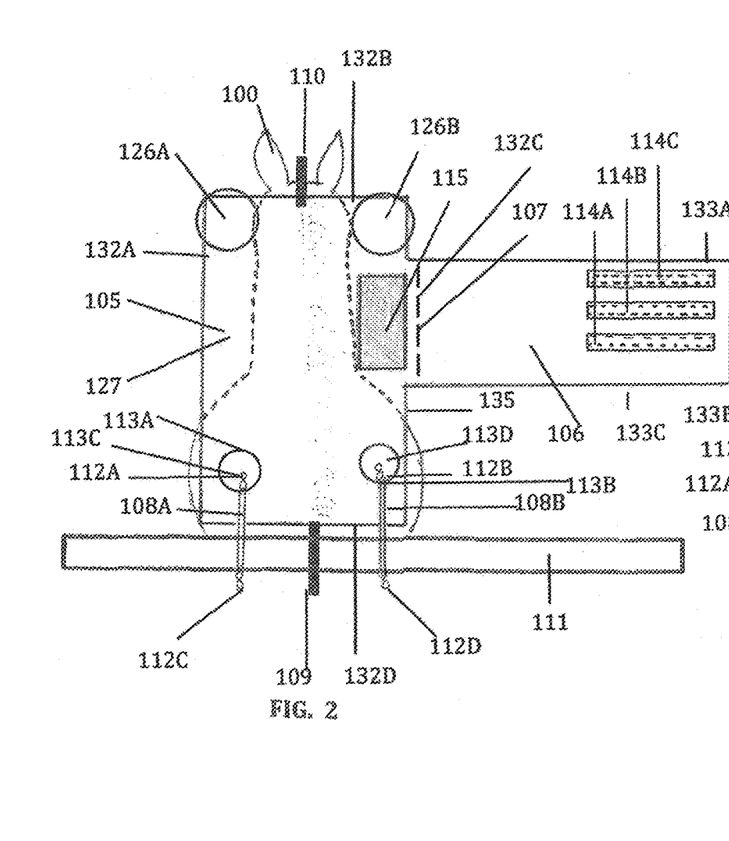
FIG. 2. is a plan view of the animal cooling wrap member of the animal cooling kit superimposed over a top view figure of a horse before the animal cooling wrap is fitted to the horse.

FIG. 2 is a plan view of the top side of an exemplary embodiment of the animal cooling wrap member, 127 superimposed over the top of horse 100, before it is fitted to the horse. Rectangular main body panel, 105 and a second body panel, 106 are separated by a dotted line 107, which represents the second side edge, 132C of the main body panel, 105 where its boundary ends and the boundary of the first edge of the second body panel, 106 begins. The main body panel, 105, has a front edge, 132D, and a rear edge of equal length, 132B positioned opposite. The main body panel, 105 has a first side edge, 132A, and a second side edge, 132C of equal measurement forming a panel suitable in length to extend from the withers, 116 (FIG. 1A) to the poll, 117 (FIG. 1A) of horse, 100. Both the main body panel, 105 and the second body panel 106 of the animal cooling wrap, 127 are made of absorbent, porous material that has an open cell, foam structure that is gas permeable, having a textured underside, 104B (FIG. 4B) characterized by evenly sized and evenly spaced dimples, 129, (FIG. 4B) which serve as capillaries and act as a conduit for heat exchange and moisture removal.

The main body panel, 105 and the second body panel, 106 are held in place indirectly to the body of horse, 100 by a plurality of removable straps, 109 and 110 which may be fabricated from but not limited to hook and loop fastener material, and or flat, nylon web material. Tack customarily worn by a horse such as but not limited to a halter or saddle (tack not shown) are intended to serve as an anchor to affix the cooling wrap member, 127 to the horse, 100. The removable girth attachment, 111 is used to attach the animal cooling wrap, 127 indirectly to the barrel, 120 (FIG. 1A) of horse 100, and serves as an anchor to which removable strap, 109 can be attached. The girth attachment, 111 by preference and not limitation is made from material of interwoven strands of rubber, having a stretched length with at least a 40 percent stretch of the original length under force, and returning to original shape after forces are removed, but any suitable material that extends around the barrel of horse, 100 will work. Hook and loop fasteners, 134A and 134B, (FIG. 6B) represent a preferred attachment method for girth attachment, 111 on to horse, 100, but any suitable method will work.

Figure 6A:
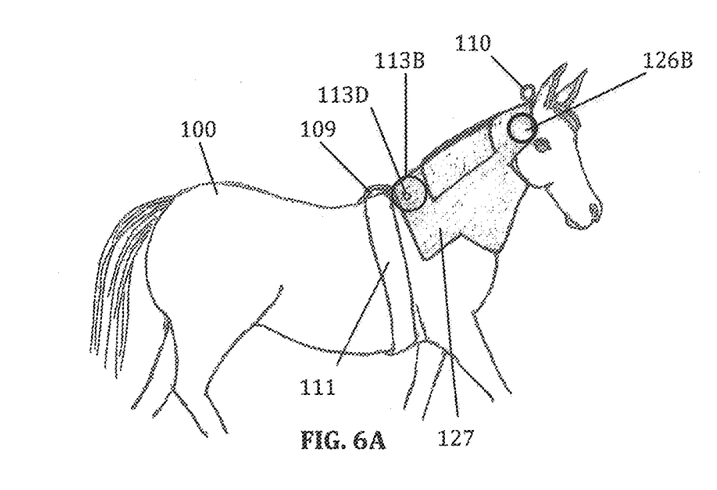
FIG. 6A is a right side view of the horse in FIG. 1A, with the animal cooling wrap member of the animal cooling kit secured to the horse, also showing a plurality of straps and fasteners.
Figure 6B:
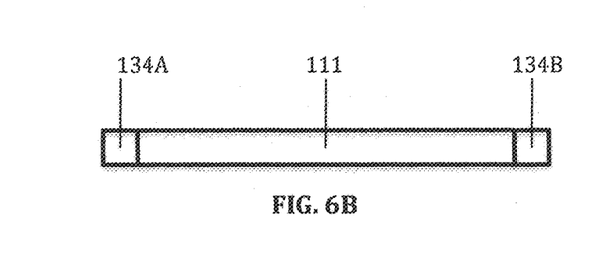
FIG. 6B is a plan view of one strap used to attach the animal cooling wrap indirectly to the horse.
Figure 6C:
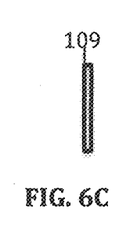
FIG. 6C is a plan view of one strap used to attach the animal cooling wrap indirectly to the horse.
Figure 6D:
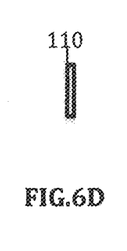
FIG. 6D is a plan view of one strap used to attach the animal cooling wrap indirectly to the horse using a piece of equipment (not shown).
Figure 6E:
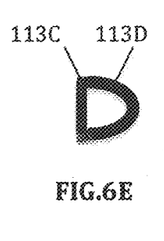
FIG. 6E is a magnified, side view of an attachment mechanism.
Figure 6F:
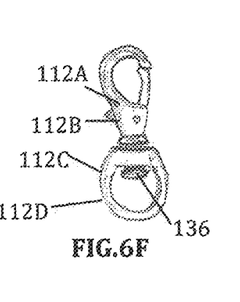
FIG. 6F is a side, close-up view of a hook.

Removable elastic straps segments, 108A (left) and 108B (right), which use but are not limited to a hook assembly 112A, of circle 113A and 112B of circle 113B, (enlarged version(s) of hooks shown in FIG. 6F), attach to and release from attachment mechanism 113C, of circle, 113A and 113D of circle 113B (enlarged version of attachment mechanism shown in FIG. 6E). Attachment mechanism, 113C and 113D, represent a preferable method of attachment, but any other suitable method serving to attach the removable elastic strap segments, 108A and 108B to the main body panel 105 will work. Duplicate hook assembly 112C and 112D can be used to connect and disconnect the removable elastic strap segments 108A and 108B to equipment worn by a horse such as but not limited to a saddle (not shown).

Guttural pouch sections of the absorbent, porous material sections 126A, 126B of the main body panel 105 are depicted by two solid line circles positioned to the right and left of the poll, 117 of horse, 100 of FIG. 1A, and represent the sections of material in the animal cooling wrap, 127 that are extended to cover the guttural pouches of 102B, FIG. 1A and 102A, FIG. 1B.

In the disclosed embodiment, second body panel, 106, has an end edge, 133B the underside of which shows a plurality of closures 114A, 114B, 114C, (attached by stitching but any suitable method of attachment will work), (depicted by broken lines), which attached to closure mechanism, 115, fastened to the top side of main body panel 105, adjacent to boundary line, 107 by stitching (but any suitable method of attachment will work). This plurality of closures 114 A, 114B, 114C, and 115 are used for securing and releasing the second body panel, 106 to and from the main body panel, 105 and may be fabricated from a preferred plurality of hook and loop fastener material, but any suitable method of opening and closing attachment will work.

A reinforcement edging, 135 fabricated by waterproof nylon or the like, and affixed by sewing or any method where it will remain in place, has been added to the perimeter of the animal cooling wrap, 127. Edging 135, serves as extra protection since although durable, the principle absorbent material is of a porous nature and not indestructible. In addition, edging 135 assists with extra weight thereby helping to keep the animal cooling wrap, 127 flat against the body of horse, 100 to facilitate continual conductive cooling.

Figure 3:
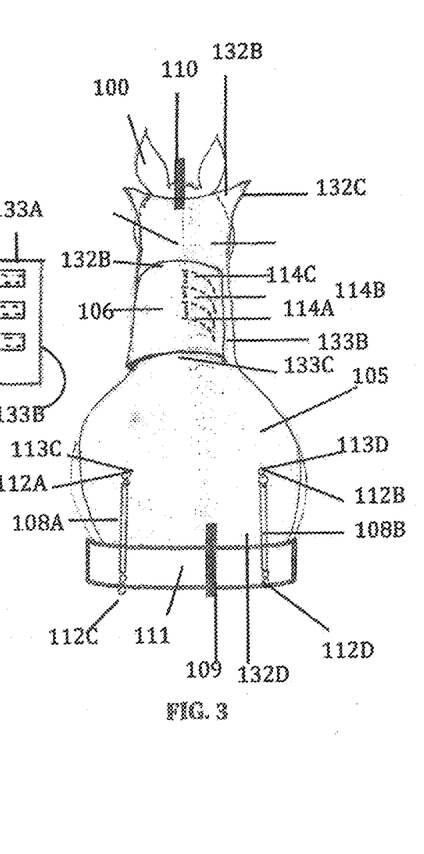
FIG. 3 is a top, view of the animal cooling wrap member of the animal cooling kit where it is shown fitted to the horse.

FIG. 3 is a top view of the animal cooling wrap member, 127 (FIG. 2) of the animal cooling kit, shown fitted to horse, 100 as one skilled in the art will consider from the perspective of sitting astride horse, 100. In the depicted embodiment, the main body panel, 105 of the animal cooling wrap, 127 beginning with front edge, 132D, has been draped longitudinally from center, equidistantly upon the left and right dorsal sections of the neck 123 (FIG. 1B) and 118 (FIG. 1A), suitable in length, not restricted by size and positioned between the withers 116 (FIG. 1A), and the poll 117 (FIG. 1A) of horse, 100. In this depiction, the animal cooling wrap, 127 is secured to the horse, 100 by way of example and not limitation using strap 109, which is by principle shown with the removable girth attachment, 111 (also shown in FIG. 6A). Removable strap, 110 and removable elastic strap segments 108A and 108B and attached hook assemblies, 112A, 112C and 112B and 112D are shown, however not assumed in use for this representation.

Main body panel, 105 is further held in place directly to horse, 100 by second body panel, 106 after it has been wrapped around horse, 100.

Depicted in the closed position, second body panel, 106 beginning with shared boundary, 107 (FIG. 2) has been stretched down and across the right ventral section of neck, 119 (FIG. 1A) towards and across the left ventral section of neck, 124 (FIG. 1B) continuing up over the left dorsal section of neck 123 (FIG. 1B) and onto the right dorsal section of neck, 118 (FIG. 1A) where it is shown attached to horse, 100 using a plurality of closures 114A, 114B, 114C located on the underside of second body panel, 106 and represented by dotted line depiction. The plurality of closures, 114A, 114B, 114C, are assumed to be attached to the closure mechanism, 115 of the hook and loop fastener material, (not shown) previously depicted in FIG. 2.

Also evident, by exemplary perspective, are the safety advantages seen in the contoured fit of the animal cooling wrap, 127 on horse, 100. One skilled in the art will notice that there are no intended parts of animal cooling wrap, 127 left unsecured or otherwise loose to catch on the external environment while in use either with a rider, or by a horse unsupervised in a stall. Also evident, is the quick release feature represented by the plurality of closures 114A, 114B, 114C, (and 115, not shown), and the ease of adjustment it represents using the preferred methods discussed, which allows the person riding the horse to remove and or adjust the animal cooling wrap, 127 by themselves with one hand, while maintaining their other hand on tack such as a saddle or reins (not shown) so as to retain continual communication with the horse, independent from relying upon the assistance of others.

Figures 4A, 4B:
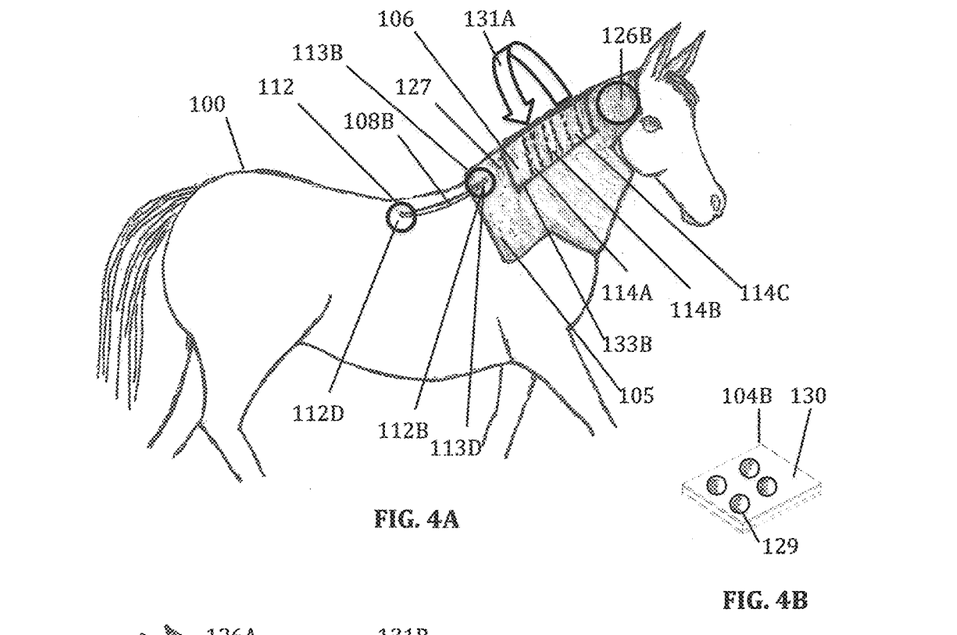
FIG. 4A is a right side view of the horse in FIG. 1A with the animal cooling wrap member of the animal cooling kit secured to the horse.
FIG. 4B is a magnified, isometric view of the underside portion of the porous material of the animal cooling wrap member of the animal cooling kit.

FIG. 4A is a right perspective, side view of horse, 100 wearing one embodiment of the animal cooling wrap member, 127 of the animal cooling kit (FIG. 2, and FIG. 7A) shown in the fastened position on horse, 100. In this disclosure, the main body panel, 105 is seen with the right, removable elastic strap segment, 108B attached to animal cooling wrap, 127 by attachment mechanism, 113D (FIG. 6E) and hook assembly, 112B (FIG. 6F) both depicted in circle, 113B. Removable right, elastic segment 108B could be attached to a saddle (not shown), by the hook assembly, 112D, depicted in circle 112.

One skilled in the art will appreciate that this exemplary depiction represents the second body panel, 106 in the closed position. As such, it should be inferred that the following steps have been executed: Second body panel 106, starting from the shared boundary 107 (FIG. 2) of the main body panel 105 (FIG. 2) and concluding with the end edge, 133B has been stretched downward and across the right and left ventral sections of neck, (119 FIG. 1A and 124, FIG. 1B) between the chest, 122 (FIG. 1A), and the throat latch, 121 (FIG. 1A) of horse 100, stretched upwards continuing in the direction of the arced arrow, 131A over the top of the neck towards one skilled in the art, where the end edge, 133B of second body panel, 106 ends, and is represented as affixed to the main body panel, 105. End edge, 133B is attached to the right dorsal section of neck 118 (FIG. 1A) using the plurality of closures, 114A, 114B, and 114C located on the under side of second body panel, 106 (FIG. 2) and depicted in this representation by dotted lines. The associated closure mechanism, 115, (FIG. 2) of the hook and loop fastener material of the main body panel, is assumed to be in use and not shown.

One skilled in the art will also notice that the right guttural pouch, 102B (FIG. 1A) from an anatomical perspective, is assumed to lay beneath the guttural pouch section, 126B of the main body panel, 105 of the animal cooling wrap, 127 represented by a solid lined circle. Constructed as such, the animal cooling wrap member, 127 of the animal cooling kit (FIG. 2, and FIG. 7A) extends to cover principle areas of horse, 100 that contribute to thermoregulation including the vascular connections, 103A and 103B (FIG. 1A), and guttural pouch, 102B, FIG. 1A.

Figures 7A, 7B:
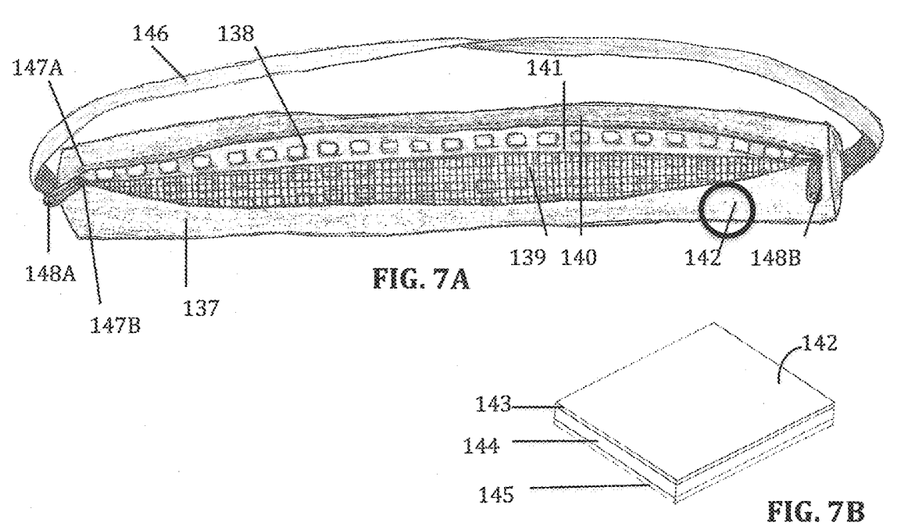
FIG. 7A is a three-dimensional view showing the standard insulated cooler and an icepack member of the animal cooling kit.
FIG. 7B is a magnified, isometric view of the layers contributing to the standard insulated cooler.

FIG. 4B is a magnified, isometric view of the textured under side portion, 104B of the porous, absorbent material, of the animal cooling wrap member, 127 of the three exemplary pieces of the animal cooling kit, (FIG. 2, and FIG. 7A). The textured underside of the absorbent, porous material, 104B of the animal cooling wrap, 127 contains regular spaced and uniform-sized, concave orifices, 129, which are less in thickness compared to the surrounding area, 130 of the same material. These tiny, evenly spaced pores, 129 act like capillaries and serve to draw up moisture and heat transferred by conduction from horse, 100 in a wicking process. The material between the dimples, 130 is of relative smooth and uniform thickness, dimensionally thicker than that of the average measurement of the material found at the apex of the dimples, and does, by design remain flat and in contact with the animal during conductive, circulatory and evaporative cooling.

Figure 5:
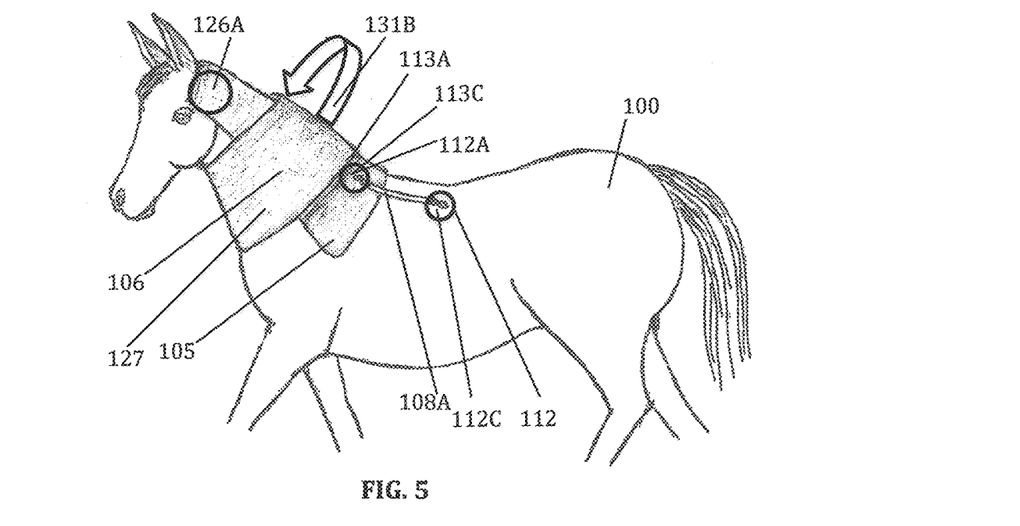
FIG. 5 is a left side view of the horse in FIG. 1B with the animal cooling wrap member of the animal cooling kit secured to the horse.

FIG. 5 is the left side view of horse, 100 and represents the opposite side of exemplary embodiment, FIG. 4A. Horse, 100 is shown wearing the animal cooling wrap member, 127 in the fastened position. The main body panel, 105 is shown with the removable elastic strap segment, 108A, attached to the animal cooling wrap, 127 by attachment mechanism, 113C (FIG. 6E), and hook assembly, 112A, (FIG. 6F) both depicted in circle, 113A. Removable elastic segment 108A could be attached to a saddle (not shown) by the hook assembly, 112C depicted in circle 112.

Arrow, 131B illustrates the end step of the directional sequence for applying the animal cooling wrap, 127 to horse, 100 in which the second body panel, 106 has been extended (depicted as arced away from those skilled in the art) from the left dorsal section of neck, 123, (FIG. 1B) between the withers 116, (FIG. 1B) and the poll, 117, FIG. 1B over and on to the main body panel, 105 where it is assumed by those skilled in the art to be fastened as expressed in FIG. 4A to the main body panel, 105. Using knowledge of the disclosure of FIG. 4A, second body panel, 106 is assumed to be positioned in the closed position as described using a plurality of closures, (not shown).

One skilled in the art will realize that a left guttural pouch, 102A (FIG. 1B) from an anatomical perspective, is assumed to lay beneath the guttural pouch section, 126A of the main body panel, 105 of the animal cooling wrap, 127 represented by a solid lined circle. Constructed as such, the animal cooling wrap member 127, of the animal cooling kit (FIG. 2 and FIG. 7A), in this embodiment, extends to cover principle areas of the horse, 100 that contribute to thermoregulation including the vascular connections 103A and 103B (FIG. 1B) and guttural pouch, 102A, FIG. 1B. Together with the disclosure, begun in FIG. 4A, FIG. 5 serves to illustrate the second side of the animal cooling wrap member 127, which considered in principle together, and added to the insulated cooler and ice pack members, (FIG. 7A) of the animal cooling kit, provide a catalyst for the autonomic selective brain cooling of a horse through conductive, circulatory and evaporative cooling.

FIG. 6A is a right side view of the horse in FIG. 4A. As illustrated, this exemplary embodiment of the animal cooling wrap member, 127 of the animal cooling kit, (FIG. 2 and FIG. 7A) includes a removable strap girth attachment, 111 positioned around the barrel, 120 (FIG. 1A) of horse, 100 where it acts as an anchor for the animal cooling wrap, 127 by using removable strap, 109. The animal cooling wrap member, 127 is shown in the closed position on horse, 100 with the guttural pouch section, 126B further kept in place and against the guttural pouch (not shown) but assumed by prior explanation to be underneath 126B, as illustrated in 102B (FIG. 1A) by removable strap, 110 with a standard halter or bridle (not shown), or any other device that fits around the head of a horse and serves as an anchor. Attachment mechanism, 113D (FIG. 6E), is recognized in circle 113B, however not used in this depiction.

Straps 109, 110 and 111 represent exemplary illustration(s) of possibility for restricting the movement of the animal cooling wrap, 127 while secured to a horse, but any suitable method of securing the animal cooling wrap 127 to the animal, that restricts the animal cooling wrap where it might otherwise shift or stop having direct contact with the horse while it is in use will work. Such examples of alternative attachment methods, substitution, and or choices, not serving as restriction in method or material(s), are standard clips, snaps, ropes, belts, ties, rigging and or surcingle.

FIG. 6B is a top, plan view of the removable girth attachment, 111. Preferred material is an elastic strap of interwoven strands of rubber, having a stretched length with at least a 40 percent stretch of the original length under force, and returning to original shape after forces are removed, but any suitable material that acts as an anchor for securing or removing the girth from around the horse will work. Hook and loop fasteners, 134A and 134B are comprised of two sections, one of hook and the other of loop material, each of suitable length and width, (attached by stitching or the like) along the ends of the removable girth attachment, 111 to provide a readily adjustable loop of material around the barrel of horse, 100. Although a preferred attachment method for the animal cooling wrap to the horse, any suitable means that serves as an anchor to secure the girth to horse, 100 will work.

One skilled in the art will appreciate that removable girth attachment, 111 and or straps, 109 and 110 have a stabilizing effect upon the animal cooling wrap, 127 when used on an animal such as but not limited to a horse during ground or air transportation from one location to another when humans are not available make adjustments to the animal, to the cooling wrap, or to the environment for hours at a time, or while the horse is left free in a stall such as during recovery from exercise or while receiving medical intervention for sickness such as fever.

One skilled in the art will also appreciate a new and unexpected advantage discovered by inventors, Kasper and Kasper during the use of this type of exemplary embodiment of the invention as follows: In an unplanned intervention on a sick horse suffering from a fever up to and including temperatures of 105.8 degrees Fahrenheit that lasted for more than two weeks, Kasper and Kasper, using this exemplary embodiment of the animal cooling wrap, discovered an enhanced thermoregulatory connection between the contoured nature of the guttural pouch sections, 126A and 126B (FIG. 2) of the animal cooling wrap, 127, the guttural pouches, 102A, (FIG. 1B), 102B, (FIG. 1A), the principle vascular pathways, 103A and 103B (FIG. 1A) of the sick horse, and the association with core body cooling and temperature reduction theory previously stated by Drs. Baptiste and Naylor. It was discovered, that the autonomic selective brain cooling of the febrile horse, including the guttural pouches, was potentiated by the design principles of the invention of the appended claims.

Through conductive, circulatory and evaporative cooling the contoured design and nature of the animal cooling wrap member, 127 which is noticed to cover the guttural pouches of the horse with sections, 126A and 126B (FIG. 2), represented a spontaneous discovery for Kasper and Kasper, which was thereafter duplicated creating results of a repetitive, three degree Fahrenheit decrease in rectal body temperature of the febrile horse, absent of pharmacological intervention.

In addition to the unexpected decrease of core body temperature, one skilled in the art will also recognize the safety advantage gained by the contoured fit of the animal cooling wrap, 127 which by the nature of the design prevents unsecured or excess material to drape unattached from the animal, where it can get caught on the environment during (but not restricted to) a horse located in the inside of a trailer during ground transportation, the interior portion of a jet stall during airplane travel, in a stall of a barn, or secured by cross-ties, therefore reducing hazardous conditions for times when the horse is not continuously supervised by humans.

One skilled in the art will notice, that in keeping with the scope and spirit of the invention, the disclosed preferred embodiment and mode of operation of the animal cooling kit invention including the animal cooling wrap, 127, insulated cooler, 137 and icepack, 138 may be extended in principle to include other modes of operation and materials such as but not limited to two portable containers preferably of plastic or the like, but anything with an impermeable membranes to hold water will work. The first closed-top container is lesser in size, suitable to hold enough water by volume to dowse the animal cooling wrap with water such that no dry material remains, and the second container suitable in size to serve as a transport device and receptacle where the animal cooling wrap, 127 can receive the water from the first container and be made wet, and the animal cooling wrap, 127 applied to a horse as previously described.

FIG. 6C is a top view of strap, 109 used for indirectly securing and releasing the animal cooling wrap, 127 to and from horse, 100 by way of attachment to strap, 111 which is secured directly to horse, 100 around the barrel 120 (FIG. 1A), as depicted in FIG. 6A. Preferred material for strap, 109 is hook and loop fastener material, and or flat, nylon web material but any suitable material that establishes a releasable, loop-type connection between animal cooling wrap, 127 and horse, 100 will work.

FIG. 6D is a top view of strap, 110 used for indirectly securing and releasing the animal cooling wrap, 127 to and from horse, 100 by way of tack customarily worn by a horse such as but not limited to a halter (not shown) and intended to serve as an anchor to affix the cooling wrap member, 127 to the horse, 100. Preferred material for strap, 109 is hook and loop fastener material, and or flat, nylon web material but any suitable material that establishes a releasable, loop-type connection between animal cooling wrap, 127 and horse, 100 will work.

FIG. 6E. is a top, magnified view of the attachment mechanism, 113C and 113D. Preferred fabrication is a welded titanium, alloy D-ring, but any suitable material and shape will work to serve as an anchor to receive the hook portion, (FIG. 6F) of the attachment assembly of the removable elastic strap segments, 108A and 108B, (FIG. 2), which serve to attach and release the animal cooling wrap, 127 to an exemplary piece of equipment such as but not limited to a saddle (not shown). The attachment mechanism is attached by stitching to the animal cooling wrap, 127 but any suitable method of attachment will work.

FIG. 6F is a magnified, side view of the hook portion, 112, A-D of the attachment assembly of the removable elastic strap segments, 108A and 108B, as stated in FIG. 6E, and shown by 108A and 108B (FIG. 2). The exemplary embodiment of FIG. 6F is illustrated by but not limited to a titanium alloy, swivel hook mechanism, 136, but any hook mechanism that serves to attach and release the elastic strap segments, 108A, 108B, (FIG. 2) from the animal cooling wrap and or anchoring devices will work.

FIG. 7A represents the first of three sequential, perspective views showing a standard insulated cooler member, 137, in an open position together with a standard icepack member, 138 depicted as fitted in to the open cooler member, 137. These two members, combined with the animal cooling wrap, 127 (FIG. 2) by way of example and not limitation represent an animal cooling kit. It is preferred that the standard ice pack, 138 be suitable in size to suitably line the interior of the insulated cooler, 137 but any size ice pack will work, as well as any other means by which cold can be transferred to the animal cooling wrap, 127. The standard insulated cooler, 137 for exemplary purpose is shown as cylindrical, but any shape insulated cooler will work provided it is an insulated encasement represented by materials that make for a poor conductor of heat.

By way of example and not limitation, a mesh fabric layer, 139 (pocket) is added to the interior of the insulated cooler, 137 by way of being stitched, glued or otherwise affixed to create a suitable mechanism, for securing and releasing the ice pack, 138. The mesh pocket, 139 is outfitted with a closing mechanism such as but not limited to hook and loop fasteners, such that the upper edge of the mesh fabric long side, 141 with the hook fabric can be pressed against one upper, long side edge of the insulated cooler, 140 with the loop fabric to create a closed pocket when pressed against each other manually with a suitable amount of pressure, until which point reverse pressure is manually added to pull opposing edges 140 and 141 apart from each other, so as to open the pocket to add, remove and or otherwise adjust the icepack. The preferred fabric mesh pocket, 139 of this exemplary embodiment is fabricated from standard, synthetic, woven fiber, constructed with evenly spaced apertures, although any material that preforms likewise will work.

FIG. 7B. is a magnified, isometric view of small segment, 142 of preferred layers contributing to a standard insulated cooler. The exemplary insulated cooler is fabricated from, but not limited to a layer of polyethylene high density, closed cell foam insulation, 144 sandwiched between the outer layer, 143 fabricated from a preferred 600 denier type polyester fabric (but any suitable denier range outside of 600 will work), and an inner layer, 145 such as but not limited to polyvinyl chloride material. The mesh fabric, 139 by exemplary design follows the inner layer, 145, of the insulated cooler member, 137 of the animal cooling kit, (FIG. 7A) and 127, (FIG. 2).

Figure 8:
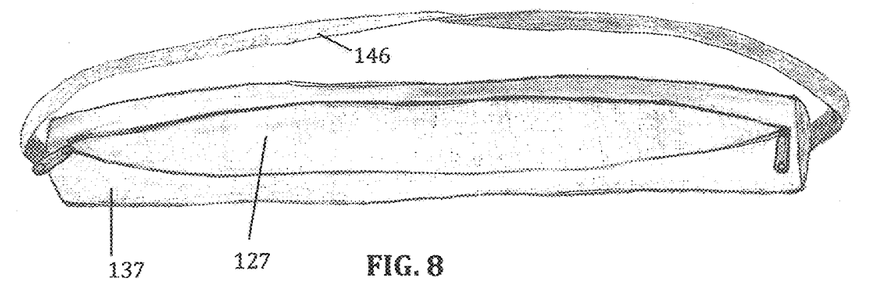
FIG. 8 is a three-dimensional view of the insulated cooler member in the open position, shown together with the animal cooling wrap member of the animal cooling kit.

FIG. 8. building upon FIG. 7A as the second of three, three-dimensional, sequential views of the standard insulated cooler member, 137, of the animal cooling kit, one skilled in the art will notice the insulated cooler, 137 in an open position and inclusive of the animal cooling wrap member, 127. This exemplary embodiment shows the animal cooling wrap, 127 depicted as having been folded into a cylindrical shape of suitable size, so as to fit by way of example and not restriction, the dimensions of the insulated cooler, 137. By way of exemplary principle, this embodiment is illustrated in cylindrical shape, but any shape will work for the insulated member, 137 of the animal cooling kit whereby a suitable icepack can be housed with the animal cooling wrap, 127 to create a counter current exchange of energy.

Figure 9:
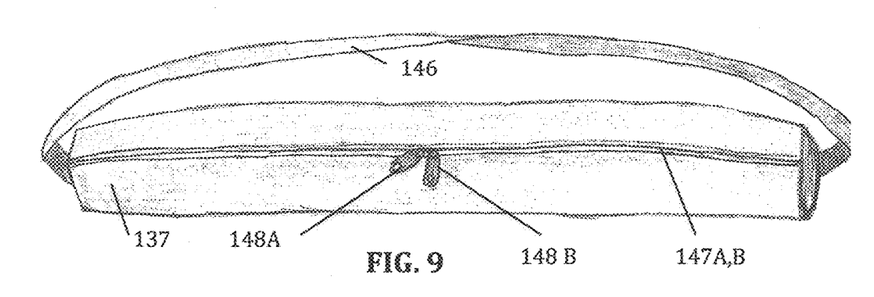
FIG. 9 is a three-dimensional view of the insulated cooler member in the closed position.

FIG. 9. further builds upon the two previous, three-dimensional, sequential views of the insulated cooler member, 137 of the animal cooling kit. In this exemplary illustration the third and final view of the animal cooling kit is depicted in the closed position. It should be apparent to those skilled in the art, that FIG. 9 illustrates an exemplary embodiment whereby both the animal cooling wrap, 127 and the ice pack, from FIG. 8 are inferred, as the preferred depiction of the design intends, to be included within the insulated cooler, 137, assumed in principle, however, not shown.

The insulated cooler member, 137 includes a standard slide fastener, (zipper), having two opposing rows of protruding teeth, 147A,B shown in an interlocked position, and (147A and 147B, FIG. 7A shown in an non-engaged position). The zipper is fabricated from a preferred, highly-crystalline, engineering thermoplastic (but any suitable material will work, which may be caused to interdigitate) thus mechanically linking the two rows of teeth, so as to increase or decrease the size of the opening of the insulated cooler, 139.

Also included are preferred double sliders, 148A and 148B, fabricated from preferred steel or zinc. These sliders are operated by hand along the rows of teeth to either join or to separate the teeth and enlarge or minimize the opening to the insulated cooler. A single slider or other suitable closure mechanism used to bind the edges of the insulated cooler will also work. Also illustrated is a strap, 146 fabricated from but not limited to a flat nylon web material suitable in size to extend from one end of the insulated cooler, 137 to the other end, (but any material in principle which allows for portability of the animal cooling kit, 137 from one location to another location will work,) and serve to illustrate the ability of the animal cooling kit to provide cold temperatures to a hot horse upon demand, inclusive of the aforementioned advantages.

While the animal cooling kit invention has been described h reference to embodiment(s) including three main exemplary members and their steps, it will be understood by those skilled in the art that adaptive measures based upon environmental requirements necessitate substitutions, changes, modification and manner of operation, to be made accordingly. As such, it is desired that the invention not be limited to the embodiments disclosed, and will therefore extend to all other embodiments falling within the scope and spirit of the appended claims.

The invention claimed is:

1. An animal cooling wrap configured for placement on a neck of a horse, said animal cooling wrap comprising:
    a rectangular main body panel having a front edge, a rear edge, a first side edge, a second side edge, a length sized and configured to extend from a withers to a poll of the horse, and a width sized and configured to cover at least left and right guttural pouches of the horse;
    a second body panel extending perpendicularly to the main body panel from the second side edge of the main body panel and spaced from the front and rear edges, the second body panel sized and configured to extend from a chest to a throat latch of the horse;
    a plurality of closures on the second body panel configured to releasably secure the second body panel to a topside of the main body panel with the second body panel encircling the neck of the horse.

2. The animal cooling wrap of claim 1, wherein the main body panel and the second body panel are made from a water absorbent, porous material.

3. The animal cooling wrap of claim 2, wherein the water absorbent, porous material has a top side that is substantially flat and a bottom side comprising a plurality of concave dimples.

4. The animal cooling wrap of claim 2, wherein the water absorbent, porous material comprises an open cell foam structure.

5. The animal cooling wrap of claim 1, wherein the main body panel further includes a strap on each of the front and rear edges extending perpendicularly thereto for indirectly securing the animal cooling wrap to the horse;
    a plurality of elastic strap segments, each elastic strap segment removably attached to the main body panel adjacent the front edge by an attachment mechanism; and
    an elastic girth attachment strap adjacent the front edge and extending parallel to the second body panel, the girth attachment strap configured to extend around a barrel of the horse.

6. The animal cooling wrap of claim 5, wherein the attachment mechanisms of each elastic strap segment, comprise a hook assembly; and wherein each of the plurality of elastic strap segments further include an additional hook assembly for releasably attaching the elastic strap segment to equipment worn by the horse.

7. The animal cooling wrap of claim 1, further including a reinforcement edging around a perimeter of the cooling wrap.

8. The animal cooling wrap of claim 7, wherein the reinforcement edging comprises nylon.

9. A kit comprising the animal cooling wrap of claim 1 and an insulated cooler configured to store the animal cooling wrap.

10. The kit of claim 9, further comprising an icepack member for placement in the cooler.

* * * * *